United States Patent [19]
Girard et al.

[11] Patent Number: 5,716,417
[45] Date of Patent: Feb. 10, 1998

[54] INTEGRAL SUPPORTING STRUCTURE FOR BIOPROSTHETIC HEART VALVE

[75] Inventors: Michael J. Girard, Lino Lakes; Todd D. Campbell, White Bear; M. William Mirsch, II, Roseville; Kristen Swanson, St. Paul, all of Minn.

[73] Assignee: St. Jude Medical, Inc., St. Paul, Minn.

[21] Appl. No.: 472,744

[22] Filed: Jun. 7, 1995

[51] Int. Cl.⁶ .................................................. A61F 2/24
[52] U.S. Cl. ..................................... 623/900; 623/2
[58] Field of Search .............................. 623/900, 2, 3, 623/66

[56] References Cited

U.S. PATENT DOCUMENTS

| | | | |
|---|---|---|---|
| 3,570,014 | 3/1971 | Hancock | 623/900 |
| 4,626,255 | 12/1986 | Reichart et al. | 623/900 |
| 4,851,000 | 7/1989 | Gupta | 623/2 |
| 5,258,023 | 11/1993 | Reger | 623/900 |
| 5,411,552 | 5/1995 | Andersen et al. | 623/900 |

FOREIGN PATENT DOCUMENTS

| | | | |
|---|---|---|---|
| 1264471 | 2/1972 | United Kingdom | 623/2 |
| 2279134 | 12/1994 | United Kingdom | 623/2 |

*Primary Examiner*—John G. Weiss
*Assistant Examiner*—Bruce E. Snow
*Attorney, Agent, or Firm*—Hallie A. Finucane

[57] ABSTRACT

A stent for receiving and supporting a tissue heart valve for ultimate implantation into a human, the heart valve including tissue leaflets joined at circumferentially spaced commissures, wherein the stent includes at least one commissure support post and at least one sinus support structure each sinus support structure being disposed between but not functionally connected to an adjacent commissure support post.

3 Claims, 4 Drawing Sheets

INTEGRAL SUPPORTING STRUCTURE FOR BIOPROSTHETIC HEART VALVE

FIELD OF THE INVENTION

This invention relates generally to replacement heart valves for use in humans, and more particularly is directed to an integral supporting structure for use in a bioprosthetic tissue valve.

BACKGROUND OF THE INVENTION

Prosthetic heart valves are typically used to replace diseased natural heart valves in either the aortic or mitral position. Several categories of prosthetic heart valves are in existence. One category includes what may be referred to as mechanical heart valves. Such valves typically have a rigid orifice ring and rigid hinged leaflets coated with a blood compatible substance such as pyrolytic carbon. Other configurations, such as ball-and-cage assemblies, have also been used for such mechanical valves.

A second category of prosthetic heart valves comprises assemblies having various amounts of biological or natural material. As described in more detail below, some of these valves include leaflets derived from natural material (typically porcine) and still include the natural supporting structure or ring of the aortic wall. In other valves, leaflets derived from natural material (typically bovine pericardium) are trimmed and attached to a synthetic, roughly annular structure or ring that mimics the function of the natural aortic wall. In still other valves, both the leaflets and the annular support ring are formed of synthetic polymers or biopolymers (e.g., collagen and/or elastin). For ease of description, these valves will be referred to herein as bioprosthetic valves.

Many bioprosthetic valves include an additional support structure or stent for supporting the leaflets, although so-called stentless valves are also used. The stent provides structural support to the cross-linked valve, and provides a suitable structure for attachment of a sewing cuff to anchor or suture the valve in place in the patient.

Bioprosthetic valves which include a stent are typically of two types. In one type, an actual heart valve is retrieved from either a deceased human ("homograft") or from a slaughtered pig or other mammal ("xenograft"). In either case, the retrieved valve may be trimmed to remove the aortic root, or the aortic root or similar supporting structure may be retained. The valve is then preserved and/or sterilized. For example, homografts are typically cryopreserved and xenografts are typically cross-linked, typically in a glutaraldehyde solution. The tissue valve may then be attached to the stent.

The other type of stented bioprosthetic valve includes individual valve leaflets which are cut from biological material, e.g., bovine pericardium. The individual leaflets are then positioned on the stent in an assembly that approximates the shape and function of an actual valve.

In the case of either type of stented bioprosthetic valve, the function of the stent is similar. Primarily, the function of the stent is to provide a support structure for the prosthetic valve. Such a support structure may be required because the surrounding aortic or mitral tissue has been removed in harvesting the valve. The support offered by a stent in a valve is important for several reasons. First of all, a valve is subject to significant hemodynamic pressure during normal operation of the heart. Upon closing the valve the leaflets close to prevent backflow of blood through the valve. In the absence of any support structure, the valve cannot function properly and will be incompetent. One function of the stent is to assist in absorbing the stresses imposed upon the leaflets by this hemodynamic pressure. This is typically achieved in existing stents through the use of commissure support posts to which the valve commissures are attached.

Some known stents have been designed such that the commissure support posts absorb substantially all the stresses placed on the valve by hemodynamic pressure. One such stent is a formed piece of spring wire which is bent to form three vertically-extending commissure support posts, each having a U-shape and being connected to the other commissure support posts via arcuate segments of wire. Such a stent is described in U.S. Pat. No. 4,106,129 to Carpentier, et al. In that stent, the leaflet stresses are borne by the commissure posts rotating around and exerting a torque upon the arcuate wire sections between the posts. The composition and structure of this stent also provides for deformability of the orifice-defining elements. A separate insert element in the form of a plastic web is positioned around the wire stent prior to attachment of the valve.

In other types of stents, the commissure posts are fixed to a rigid base and are designed to be substantially flexible along their entire length so that the posts bend in the manner of a fishing pole in response to the stresses imposed upon the leaflets by hemodynamic pressure. An example of such a stent is shown in U.S. Pat. No. 4,343,048 to Ross, et al.

Other stents, for example the stent shown in U.S. Pat. No. 4,626,255 to Reichart, et al., include further support structure connected to and disposed between the commissure support posts. Such support structure prevents a given commissure post from being resilient along its entire length. Still other stents, such as in U.S. Pat. No. 5,037,434 to Lane, include an inner support frame with commissure posts resilient over their entire length, and a relatively more rigid outer stent support which begins to absorb greater stress as the associated commissure support bends further inward.

Although all of these stents provide support to the bioprosthetic valves to which they are attached, the stress distributions are often unnatural, leading to premature wear or degradation of over-stressed portions of the valve. Accordingly, the need exists for stents which more closely approximate the stress response of a natural aortic or mitral valve. Furthermore, the stents which include several parts are mechanically complex and require multiple assembly steps. A stent which includes a stress response that approximates a natural valve would thus also desirably have an integral construction.

Another function of a stent is to serve as a framework both for attachment of the valve, and for suturing of the valve into place in the recipient, e.g., a human patient. Toward that end, the stent, or a portion of the stent, is typically covered with a sewable fabric or membrane, and may have an annular sewing ring attached to it. This annular sewing ring serves as an anchor for the sutures used to attach the valve to the patient.

A variety of different stent designs have been employed in an effort to render valve attachment, and implantation of the valve simpler and more efficient. Design trade-offs have often occurred in designing these stents to have the desirable stress and strain characteristics while at the same time having a structure which facilitates assembly and implantation.

In the stentless valves previously referred to, the unsupported valve is sewn into the recipient's aorta in such a way that the aorta itself helps to absorb the stresses typically absorbed by a stent. Current porcine aortic stentless valves, such as porcine aortic stentless valves, are typically intended for use in the aortic position and not in the mitral position. A mitral valve would require a support structure not presently available with porcine aortic valves, and recently, stentless porcine mitral valves for placement in the mitral position have been developed.

Indeed, the stented valves used in the mitral position utilize the stent to provide support for normal valve function. In these stented mitral valves, a "low profile" stent having generally shorter commissure posts has been used, so as to prevent the ventricle wall from impinging on the valve. However, use of a lower profile stent often requires that the bioprosthetic valve be somewhat distorted upon attachment to the low-profile stent. This, in turn, can lead to reduced functionality of such valves. While the "higher profile" stents can avoid this distortion, care must be given to valve placement so as to avoid the referenced impingement by the ventricle wall. A need exists for a stent for use in the mitral position that includes the advantageous stress/strain and attachment characteristics previously described.

Known stents for bioprosthetic valves have been formed from a variety of materials including both metals and polymers. Regardless of the material employed, the long-term fatigue characteristics of the material are of critical importance. Unusually short or uneven wear of a stent material may necessitate early and undesirable replacement of the valve. Other material characteristics are also considered in selecting a stent material, including: rate of water absorption, creep, and resilience to the radiation which may be used for sterilization. Further, it may be highly desirable to form the stent of a radio-opaque material to allow the stented valve to be viewed by x-ray imaging. Of course, the selected material must also be biocompatible and have the required physical characteristics to provide the desired stress/strain characteristics. Furthermore, most existing stents are formed of a material having a constant cross-sectional dimension. Formed wire stents and stents formed from stamped metal are examples. Use of a material of variable cross section would allow stress and strain characteristics to be carefully controlled by adding or subtracting cross sectional area in certain regions of the stent, as may be required.

SUMMARY OF THE INVENTION

Accordingly, it is a general aim of the present invention to provide an improved stent for use in combination with bioprosthetic heart valves. Any valve or leaflet, whether mechanical or natural tissue, may be used with the stents of the present invention. Typical natural valves include, but are not limited to horse, kangaroo, rabbit, bear, cow, pig, boar and human. The preferred valve or leaflet is porcine-derived.

In accordance with that aim, it is a primary object of the present invention to provide an integral stent that more closely approximates the stress and strain response of a natural valve than has been provided by known stents.

It is a related object of the invention to provide such a stent that closely mimics the natural valvular anatomy and allows the three commissures of the valve to work in unison.

It is a further related object to provide such a stent having adequate support in the commissure region, while approximating the constraints placed on the valve by the natural compliance of the aorta.

A further object of the invention is to provide an integral stent having the desirable stress-strain characteristics, and having a structure that facilitates assembly of the valve to the stent. It is another object of the invention to provide a stent having a structure that facilitates the implantation of the assembled valve in the patient. It is a related object of the invention to provide such a stent with easy and complete commissure attachment.

It is further related object to provide such a stent that allows easy attachment of the other components associated with the stented valve including the sewing ring.

A further object of the invention is to provide an integral stent composed of a material that has improved performance characteristics, particularly, superior long-term performance characteristics.

An integral stent for use in a bioprosthetic valve in accordance with the present invention achieves the aforementioned object.

The stent includes a plurality of commissure support posts, preferably asymmetrically circumferentially spaced to duplicate or approximate the spacing between valve commissures that occurs in nature. Each commissure support post includes an inflow edge, an outflow edge, and side rails connected between the edges. The side rails and edges preferably enclose a longitudinally-extending central opening that allows attachment of the commissures of the valve to the commissure support posts. In some embodiments of the invention, the stent also may include inflow rail segments connected between the inflow edges of the commissure support posts. See, for example, FIGS. 1 and 4. The inflow rail segments and the inflow edges of the support posts form a circumferentially continuous annular inflow surface.

In other embodiments of the invention, the inflow surface and the inflow rail segment may be discontinuous. In this embodiment of the invention, for example, the area between and under the commissure support posts may be open or substantially open. An exemplary embodiment of an open stent is shown in FIG. 3.

The stent may also include one or a plurality of sinus support structures. Each sinus support structure is disposed between adjacent commissure support posts. In preferred embodiments of the invention, the sinus support structure(s) are not functionally connected to the adjacent commissure support post. See, for example, FIGS. 3 and 4. As used herein, functionally connected refers to no connection, or a connection that does not share or relieve stress distribution with the support post, as described in more detail below.

In accordance with the present invention, each of the sinus support structures typically include a pair of diverging side arms. A first side arm is attached to the inflow rail and extends toward, but does not functionally connect to, one of the adjacent commissure support posts. A second side arm is also functionally attached to the inflow rail and extends toward, but does not functionally connect to, the other adjacent commissure support post. Connecting the pair of diverging side arms is a top rail which curvedly extends between the pair of side arms. One or more supports may connect the top rail to the inflow rail.

The resulting structure closely approximates the stress-strain response and dynamics of a natural valve. The commissure support posts are preferably flexible along their entire length and can form an arcuate bend, e.g., in the manner of a fishing pole.

In devices according to the present invention, in attaching the valve to the stent, tissue of the valve may connect the commissure support posts and the intermediate sinus support structures. As a result, the commissure support posts and the sinus support structures offer two different mechanism for absorbing the hemodynamic stress imposed upon the leaflets. The result is a more accurate approximation of the stress performance of a natural valve, since the sinus support regions and the means by which they are attached to the valve, mimic the constraints placed on the valve by the natural compliance of the aorta. As a result, the individual commissures work in unison and are made dependent upon each other. Furthermore, the stent is integrally formed and includes a relatively open structure; these features, among others, ease attachment to other parts of the valve, and the implantation of the completed assembly is easier and more reliable.

Other objects and advantages will become apparent from the following detailed description and appended claims, and upon reference to the accompanying drawings.

DETAILED DESCRIPTION OF THE PREFERRED EMBODIMENTS

Figure 1:
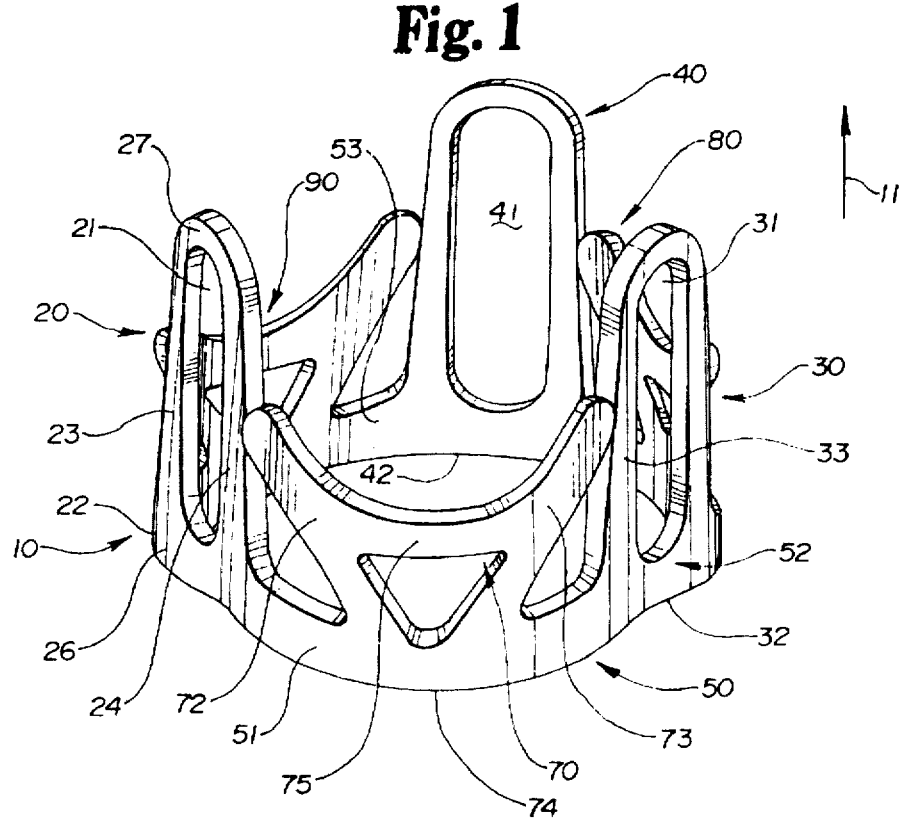
FIG. 1 is a perspective view of a stent according to one embodiment of the invention.

Turning now to the drawings, FIG. 1 shows an integral tissue valve stent 10 according to one embodiment of the present invention. As a point of reference, arrow 11 shows the direction of blood flow through the stent and valve. The stent 10, as illustrated, includes three commissure support posts 20, 30 and 40. It is intended that the invention should not be limited by the number of commissure support posts. The number used is primarily a product of the number of leaflets being used. For example, there are typically three porcine-derived leaflets, so the stent would typically include three commissure support posts. Other systems may have a difference number of leaflets, and mechanical systems typically have one to three leaflets. Also, the placement of the valve, e.g., aortic or mitral, may dictate the number of leaflets used.

According to one aspect of the invention, these support posts are asymmetrically circumferentially spaced about the generally cylindrical stent 10. It will be appreciated that support posts 20, 30, 40 are each adapted to receive a commissure of the bioprosthetic valve. Each support post includes a central opening 21, 31, 41 that runs along the length of the respective support post. The central opening as shown is preferably oblong, but any shape may be used. Also, each support post may include more than one central opening. Each oblong central opening may be bordered on either side by side rails, preferably tapered side rails. FIG. 1 shows first side rail 23 and second side rail 24. The remainder of the oblong central opening 21 is bordered by an inflow edge 26 and an outflow edge 27. The inflow edge and/or an upstream portion of the commissure support post may also include radially thickened areas. These radially thickened areas may provide additional structure as needed to avoid, channel, distribute, or reduce stress caused during operation of the valve assembly. In attaching the tissue valve to the stent, sutures would pass through the central openings. One skilled in the art will thus appreciate that the presence of these central openings facilitates attachment of the valve.

Figure 3:
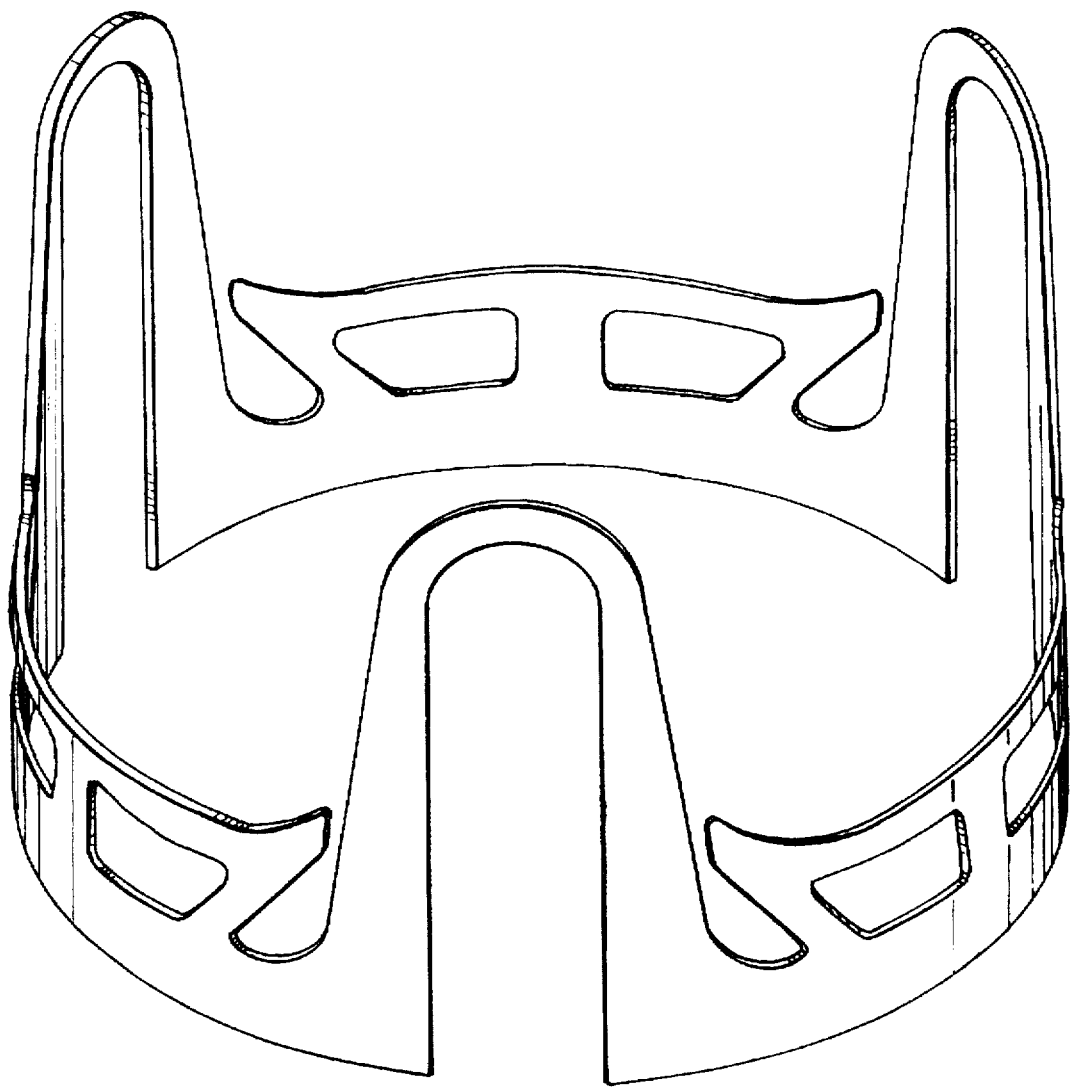
FIG. 3 is a perspective view of a stent according to another embodiment of the invention.

In a preferred embodiment of the invention, each of the side rails 23, 24 may also taper from the inflow edge to the outflow edge. This taper helps distribute stress more evenly and provides the support post with some of its advantageous functional features, as will be discussed in greater detail below. The three support posts, each having side rails, an inflow edge, and an outflow edge, are connected together by inflow rail segments 51, 52 and 53. The inflow rail segments and the inflow edges of the three support posts 20, 30, 40 may form a circumferentially continuous inflow surface 50, as shown in FIG. 1, or may be discontinuous, as shown in FIG. 3.

According to an embodiment of the invention, the inflow surface may be planar or may be scalloped to match or approximate the aortic or mitral valve anatomy. As shown in FIG. 1, the inflow surface 50 may be sinuous or sinusoidal, with each support post 20, 30, 40 having a corresponding downstream directed maximum 22, 32, 42, respectively. The area corresponding to a maximum is also the area where the greatest amount of material is removed when the stent is produced using a laser machining process, as explained in more detail below. Between each maximum is a downstream directed minimum 74, 84, 94, respectively. Likewise, each sinus support structure 70, 80, 90 has a corresponding downstream-directed minimum 74, 84, and 94, respectively. The area corresponding to a minimum is also the area where no material is removed, or the smallest amount of material is removed, when the stent is produced using a laser machining process, as explained in more detail below.

Figure 2:
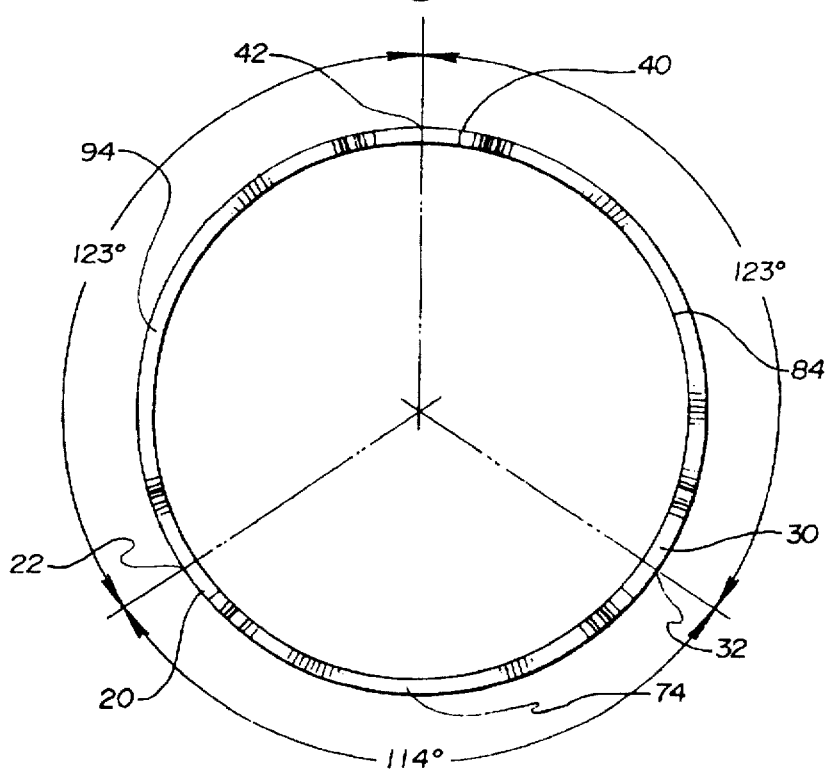
FIG. 2 is a top representative view of the relative placement of the commissure support posts according to some embodiments of the invention.

As shown more clearly in FIG. 2, an embodiment of the invention includes spacing commissure support posts 20, 30, 40 in a predetermined circumferential or angular distribution. In a preferred embodiment of the invention, support post 20, 30, and 40 are asymmetrically distributed, with only one support post being equi-angled or equidistant to the others. For example, for porcine-derived valves, the right cusp and the left cusp are typically about the same size, and the non-coronary cusp is typically smaller than the other two. FIG. 2 shows support post 40 equidistant from both support post 30 and support post 20, but neither support post 30 or support post 20 are equidistant from the other two posts. Example 1 provides various factors involved in choosing a specific support post distribution. The primary factors are the number of leaflets, the typical size of the leaflets, and the source of the leaflets. For example, porcine-derived valves typically have three leaflets, with two usually being larger than the other. To most closely approximate the spacing of the natural valve, a porcine-derived replacement valve may have two leaflets spaced from about 121° to about 125°, preferably from about 122° to about 124°, and most preferably approximately 123°. As one skilled in the art will appreciate, this spacing may change according to the nature of the actual leaflet chosen.

For example, when implanting porcine valves, it may be desirable to evaluate the specific porcine valve geometry in comparison to the recipient heart sinus region in order to match stent post height and width, and sinus height and width, etc., in order to more closely match the porcine geometry to the recipient's geometry and to avoid or minimize blocking the patient's ostium or ostia.

In accordance with the invention, one skilled in the art may also distribute stress/strain resistance by choosing a predetermined post stiffness. Post stiffness is partly a product of the size, shape, and materials used in a particular stent, in support posts 20, 30, and 40, and in their respective side rails. Stress resistance and/or distribution may also be a product of the interaction of the various structures of a stent or stent assembly according to the present invention. As described above, tapering the side rails of each post also helps distribute stress through the support post more evenly. Example 2 provides various factors involved in choosing post stiffness. It will be appreciated by those skilled in the art that selecting a maximum stress well below the endurance limit of the material prevents premature failure of the stent. For example, in a stent made from polyetheretherketone, a post stiffness from about 0.59 N/mm to about 0.73 N/mm has been found acceptable.

A stent according to the invention may also include a fabric covering or wrap, and/or a sewing ring or cuff. The construction, design, and placement of these features are well-known in the art.

The support post geometry and angular distribution noted above can adequately handle the stress and strain imposed upon the stent by the operating valve. Stent 10 also includes sinus support structures 70, 80, 90 in the sinus regions between support posts. It will be appreciated that these open-structured sinus support structures facilitate the physical attachment of the valve to the stent. As would be evident to one skilled in the art, the base of a leaflet would be attached to the fabric covering the stent approximately in the curve from the downstream end of a commissure support post, across a side arm of the adjacent sinus support structure, across the trough between two side arms, up the other side arm of the sinus support structure, and over to the downstream end of a second commissure support post. This roughly corresponds to an arced region running from the downstream distal end of a commissure support post, into the trough formed by the sinus support arms, and up to the downstream distal end of another commissure support post.

The sinus support structures also place constraints on the stented valve that allow it to perform more like a natural valve as constrained by the surrounding tissue, e.g., an aortic valve constrained by the aorta. As opposed to known stents that permit the leaflets or cusps to function independently of each other, a stent according to the present invention mimics naturally occurring heart valves by tying the function of one leaflet to the function of another. In an assembled stent of the present invention, the leaflets all function together. Pressure, stress, or constraints on one leaflet will be shared or affect another leaflet.

Figure 4:
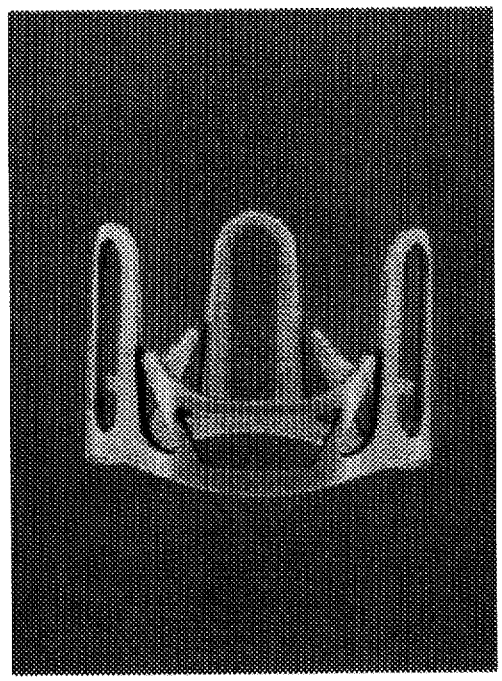
FIG. 4 is a photograph of a stent according to the embodiment of the invention shown in FIG. 1.

In an embodiment of the invention shown in FIGS. 1 and 4, each sinus support structure 70, 80, 90 is composed of two side arms 72, 73 (only the side arms for sinus support structure 70 are labelled). Each diverging side arm has a first end attached to an inflow rail segment, and a second end extending toward, but not connected to, an adjacent commissure support post. For example, sinus support structure 70 has first side arm 72 and second side arm 73, both of which have an end attached to inflow rail segment 51. First side arm 72 extends toward side rail 24 of adjacent support post 20, and second side arm 73 extends toward side rail 33 of adjacent support post 30.

Each sinus support structure may also include a top rail 75 connected to and extending between the diverging side arms 72 and 73, and, as is shown in FIG. 3, one or more additional posts may connect the top rail to the inflow rail segment.

In accordance with a preferred embodiment of the invention, the side arms are not functionally connected to the adjacent support posts to which they are closest. As noted above, if there is any minimal connection, it is preferred that such connection does not affect the natural stiffness of the adjacent support post, nor do the arms affect the stress response of the free-standing stent. It will be appreciated, however, that the presence of a tissue valve sutured to the stent provides an indirect tissue connection between a given support post and an adjacent side arm.

This indirect tissue connection is believed important for several reasons. In the case of sinus support structure 70, the indirect tissue connection between support post 20, sinus support structure 70, and support post 30 places a constraint condition on movement of the two support posts 20 and 30. Indeed, all three support posts 20, 30, and 40 are similarly constrained by the presence of the other two sinus support structures 80 and 90. This constraint causes the three support posts to act in unison when the valve is properly attached to the stent. That is, as hemodynamic pressure is applied to the valve and transferred to the stent, the indirect tissue connection causes the three support posts to work in unison, as constrained by the tissue connecting the commissures, and as also constrained by their connection to the sinus support structures. Such constraint, causing the three commissures to work in unison, is present in a natural valve. In a natural valve, this natural constraint is provided by the structure and compliance of the surrounding tissue. For example, it may be desirable to have an even higher commissure post flexibility, then have a sinus ring side arm connected to the commissure post for the additional stiffness. This may be accomplished by having a stiff side rail and no contact with the side arm, or by having a flexible side rail that is made more stiff by connection with a side arm.

In accordance with the invention, the commissure support post or posts are preferably flexible along the entire length of the side rails. In this and the embodiments noted below, it may be desirable for the commissure support post flexibility to approximate the physiological flexibility of the natural valve. It may also be desirable to minimize tissue or leaflet stress in the assembled valve, particularly under conditions when physiological flexibility can not be achieved.

In other embodiments of the invention, the commissure support post or posts may have a predetermined flexibility characteristic along its length, or may have a predetermined flexibility characteristic that is variable along its length. Areas of greater or lesser flexibility may be achieved, for example, by using different thicknesses of the same material, or by using materials of different flexibility as a composite.

In contrast, however, following harvesting of a bioprosthetic valve, the aortic root is trimmed to adequately expose the valve to allow for attachment of the valve to the stent. As such, the portion of the aorta which would normally provide this constraint is typically missing. Moreover, for placement of a bioprosthetic tissue valve in the mitral position, there is no surrounding vascular anatomy which would provide the necessary constraint. The sinus support structures 70, 80, 90 and the indirect tissue connection are therefore believed to mimic the constraints placed on the valve by the natural compliance of the aorta, without interfering with the stress/strain characteristics of the free-standing commissure support posts.

Furthermore, the preferably open geometry of the sinus support structures facilitates the assembly process, during which the tissue valve is typically sutured or attached to the fabric covering the stent, and a sewing ring is typically sutured or attached to the fabric covering the stent. It will be appreciated that the assembly process is also facilitated by the preferred integral or unitary structure of the stent. Since multiple parts do not need to be assembled to each other or to the valve, the complexity of the assembly process is reduced. An integral or unitary design also prevents relative movement between separate stent segments which may lead to placing undue stresses on the tissue valve. Similarly, it will be appreciated that the integral design provides a more constant and predictable stress-strain response since relative movement between non-integral parts would affect these characteristics.

A stent made in accordance with the present invention may also include a base ring or portion having greater radial flexibility. An example of such a stent is shown in FIG. 3. In such an alternative stent, the commissure support posts have two side rails, preferably tapered, and a closed downstream end. The upstream end of the post is open. A bioprosthetic stent comprising a ring having a central bore, at least three outwardly extending projections, the projections being spaced asymmetrically and circumferentially on the ring in each projection comprising tapered side rails.

A stent according to the invention may also include a fabric covering or wrap, and/or a sewing ring or cuff. The construction, design, and placement of these features are well-known in the art.

While a stent according to the invention may be produced from any biocompatible material, e.g., material compatible with blood and/or tissue, practical considerations dictate that consideration be given first to the use of commercially medically available materials. The stents made in accordance with this invention may be formed or pre-formed, for example, from any metal, synthetic polymer, or biopolymer capable of functioning as a stent, or may be a composite of materials, such as two or more of the above-noted polymers. Also, it may be desirable to expose the material to radiation, to gas plasma, or to an electron beam. The preferred materials may be exposed to these energy sources without significant or excessive adverse affects. The invention should not be limited by the material used to construct the stent, and should include mixtures, blends, and/or copolymers of the materials noted above.

Suitable synthetic polymers for use as a stent include, but are not limited to thermoplastics, such as polyolefins, polyesters, polyamides, polysulfones, acrylics, polyacrylonitriles, and polyaramides. Examples, include, but are not limited to polyetheretherketone (PEEK).

Suitable biopolymers are natural biomolecules that have a repeating or polymer-like structure, including but not limited to collagen, elastin, and mixtures or composites thereof.

Suitable metals include, but are not limited to, cobalt, titanium, and alloys thereof. For example, an alloy sold under the trademark Eligiloy® is a cobalt-chromium-nickel-molybdenum-iron alloy (ASTM F1058).

Although the surface of the stent may remain untreated, the stent or part(s) of the stent may be treated to effect a desired result, as, for example, to make the stent more effective within the environment of the heart. For example, the stent (or a portion of the stent) may be surface modified to increase its wetting surface tension, to increase its resistance to the harmful effects of some sterilization protocols, or to ease production of the stent. Preferred materials are synthetic, polymeric materials, and most preferred are materials that can be injection molded. The selected material needs to have both the required stress and strain characteristics as well as good long term mechanical stability. Certain metals, such as Eligiloy® may be advantageously used, as well as various polymers or biopolymers. PEEK is known to have mechanical properties in the desirable range, including a tensile strength of 14.5; a flexural modulus of 594.5; and a flexural strength of 24.65 (all in ksi at 73° F.). PEEK is also advantageous in that it has a high fatigue endurance limit, a low rate of creep, a low rate of water absorption at equilibrium, and significant radiation resiliency for the purposes of sterilization. At present, the most desirable starting material for use in forming a stent according to the present invention is PEEK 450G, commercially available from Victrex, 475 Creamery Way, Exton, Pa.

The preferred method for forming PEEK or other possible stent material into the stent, according to the present invention, is by means of injection molding. It will be appreciated that injection molding is desirable as it provides significant design flexibility. Injection molding permits construction with variable cross-section dimensions. This may be desirable if a particular portion of a stent were to require a larger stress/strain resistance characteristic. As has been discussed above, many existing stents are formed of constant cross-sectional material such as wire or stamped metal, and as such, it is difficult or impossible to design enhanced characteristics in certain portions of the stent. The flexibility of injection molding allows the cross-section of a region of the stent to be selectively increased.

It will be further appreciated that a variety of other techniques may be used to form a stent according to the invention, as dictated by the starting material. An example of an alternative technique is machining a hollow cylindrical blank. Laser machining has been found effective and is suitable for use with some of the materials mentioned above, such as Eligiloy®, PEEK, and other thermoplastics. Laser machining of some of these starting materials, such as PEEK, may require an additional surface cleaning step in order to remove some undesirable consequences of machining, such as the accumulation of carbonized plastic residue on the laser cut surface or any sharp edges.

A typical technique for surface finishing high temperature thermoplastics following laser machining is a two step process. First, the charred areas are cleaned using standard industrial grit and bead blasting equipment, such as is sold under the trademark TRINCO® by the Trinity Tool Company of Fraser, Mich. Following this char removal, the stent is tumbled in a vibratory tumbler to round and deburr the exposed edges of the stent and to prevent abrasion to the cloth covering that will eventually be fitted over the stent. Use of this process on the stent results in a superior finish, provides easier valve attachment, and reduces the chance of puncturing or tearing the valve or the cloth covering.

Although a stent of the present invention may have a substantially uniform density, stiffness, and/or resistance to stress, it may be desirable to construct a stent having zones of different characteristics. For example, it may be desirable to form the inflow rail segments of higher density and increased stiffness in comparison to a commissure support post. In another example, it may be desirable to have a downstream or distal portion of a commissure support post with less flexibility (or greater stiffness) than an upstream portion. These alternative characteristics may be chosen in order to achieve a desired result, as noted above, as well as other considerations.

Stents in accordance with the present invention may be designed to achieve practical and economic construction, convenience of use, convenience of construction and sterilization, and increase resistance to degradation in the environment of its intended use.

Stents in accordance with the present invention are preferably pre-formed to controlled dimension and characteristics prior to assembly in order to form an integral or unitary unit. Pre-forming, by injection molding, for example, eliminates and/or distributes stresses under normal conditions of use. Pre-forming in a unitary design typically leads to devices having longer service life and increased ease of construction and implantation. Furthermore, pre-forming enhances the proper positioning of the commissure support posts and of the sinus support structures. Such benefits are typically not available to structures having multiple parts or of structures that are not of unitary design.

Figure 5:
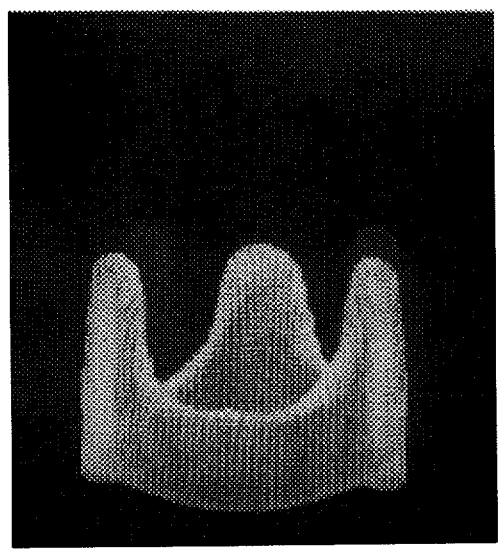
FIG. 5 is a photograph of a stent according to an embodiment of the invention showing a stent covered with a sewable fabric.

A stent according to the invention may also be covered in fabric in order to assist in attachment of the valves to the stent, to assist in placement of a sewing cuff to the stent, and to promote recipient tissue growth in and around the stent once the bioprosthetic valve has been inserted in the recipient. An exemplary stent covered with fabric is shown in FIG. 5. Various fabrics may be used, as is well known by those skilled in the art, including, but not limited to a polyester, such as Dacron®, or a polytetrafluoroethylene, such as Teflon®.

In accordance with the invention, the fabric covering may be of one-piece, as shown in FIG. 5, or may be formed of multiple pieces. In some embodiments of the invention, the fabric piece or pieces may be applied to portions of the stent, for example, in a region that is likely to be used for suturing a valve leaflet to the stent. In a preferred embodiment of the invention, the fabric covers the entire stent.

Figure 6:
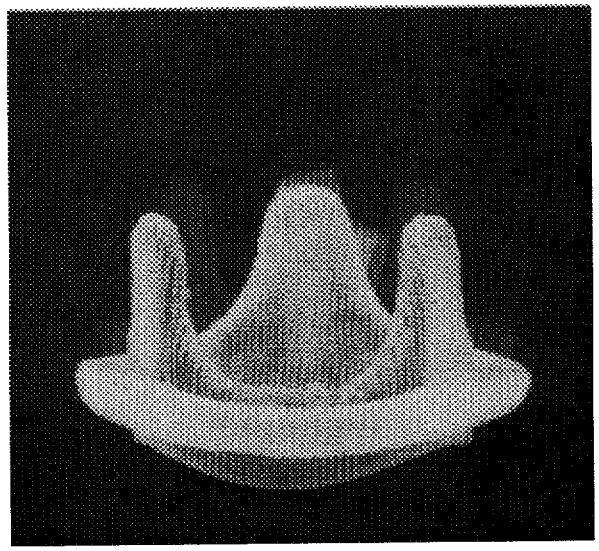
FIG. 6 is a photograph of a stent of FIG. 5 showing the attachment of the sewing ring.

In accordance with the invention, the stent, covered with a fabric, may also include a sewing ring or cuff positioned along an outside circumference of the stent. For example, see FIG. 6. In a preferred embodiment of the invention, the sewing cuff is permanently attached to the stent or to the fabric-covered stent. The stent may include one or more grooves, projections, or the like in order to assist in positioning the sewing cuff. The sewing cuff may be mounted to the stent near an upstream portion of the stent or may be placed further downstream, depending on the application. For example, for a mitral valve, it may be more desirable to position the sewing cuff in a downstream position, allowing the valve to be placed in a mitral position in the recipient without significant ventricle wall impingement. Sewing cuff placement in part determines whether the bioprosthetic valve is low profile or high profile.

In accordance with the invention, a stent assembly may include the stent covered with fabric; the fabric covered stent with a sewing ring; or the fabric covered stent with or without a sewing ring, and having the valve leaflets sutured or attached in their proper position.

In accordance with the invention, a kit may include one or more of the stent assemblies described above, plus one or more of the following: a sealed, sterilized package; a valve holder; holder handles; sizers; suture material; a needle; a scalpel; and a sterilizing solution.

EXAMPLES

Example 1

To increase the ease of valve attachment, and to limit undue stress on an attached valve, the commissure support posts 20, 30, 40 according to the invention have a particular circumferential or angular distribution. As shown more clearly in FIG. 2, the centerline of commissure support post 20 is separated from the centerline of support post 30 by 123°. The centerline of support post 30 is also separated from the centerline of support post 40 by 123°. However, the centerline of support post 20 is separated from the centerline of support post 40 by only 114°. This asymmetrical angular distribution was derived from a statistical analysis of a wide sample of porcine tissue valves. One source of such data was a compilation from the 1992 ASAIO meeting (American Society for Artificial Internal Organs). In that compilation, the attached edge length and area of each valve leaflet in a sampling of porcine valves was measured. The attached edge length was used to determine the average angular distribution of the commissures. Data was also derived from a table found in the *Annals of Thoracic Surgery*, 8:409 (1969). That table included data on the percentage of leaflet contribution relative to circumference for porcine valves. The resulting angular separation from these two measurements were then averaged to arrive at a right coronary angular separation of 123.7°, a left coronary separation of 122.8°, and a non-coronary separation of 113.4°. Given the close similarity between the right and left coronary valves, it was determined that their angular position would be set to an intermediate value of 123°, hence the placement of the posts in the stent of FIG. 2.

It will also be appreciated by those skilled in the art that this angular distribution represents an average of a variety of porcine valves, and the registration between commissure support posts 20, 30, 40 and the actual commissures for valves implanted on the stent 10 will be much higher than if equally spaced commissure posts were employed, as is typical with known stents. In that case, with a 120° separation between each support post, a given commissure could be offset from its commissure support post by several degrees. It will be appreciated that when there is a significant angular separation between a given commissure and its support post, undue stresses, and unnatural functioning of the valve may result. By using the average values according to this invention, this problem can be avoided. Any angular deviations between commissures and support posts are likely to be small, and the negative performance characteristics related to evenly (120°) spaced support posts will be minimized.

Example 2

The configuration of the stent posts 20, 30, 40, and their connection to the inflow rail segments 51, 52, 53 according to the invention, also gives each commissure post advantageous stress/strain characteristics. Based on testing and finite element analysis of the post stiffness of existing stents, a target post stiffness of 0.60 N/mm was chosen. Data was obtained by conducting deflection tests on existing stents subjected to peak physiological pressure of 250 mmHg. For a stent subjected to this peak physiological pressure, the post deflections in the radial direction, measured on the outside surface of the fabric at the top of the stent post, were derived. A radial deflection force was then directly applied to the same stent post to determine the radial force necessary to move the post to the same displacement. The necessary radial force was then divided by the measured displacement to determine a post stiffness. The 0.6 N/mm chosen target was derived as an average of these measurements. Once the post stiffness was chosen based on these measurements, the cross sectional dimensions of the commissure posts were chosen both to meet this stiffness requirement, and to meet stress requirements. The stresses obtained from imposing peak physiological displacements at the top of the post were limited to one half the endurance limit of the material chosen. The geometry of stent posts 20, 30, 40 thus have a post stiffness of 0.6 N/mm while exhibiting stress levels well below their endurance limit during application of peak physiological displacements at the top of the post.

There has thus been disclosed an integral stent including novel design characteristics resulting in a structure closely approximating the stress-strain response of a natural valve. At the same time, the stent includes features which facilitate attachment of the valve and subsequent implantation into a patient. The stent is also formed, by a variety of techniques, of a material which has very desirable mechanical properties. The invention, however, is not limited to the disclosed embodiments, but rather covers all modifications and equivalents included within the scope of the following claims.

What is claimed is:

1. A stent for receiving and supporting a heart valve for ultimate implantation into a human, the heart valve including leaflets joined at circumferentially spaced commissures, the stent comprising:

a plurality of circumferentially spaced commissure support posts, each commissure support post including an inflow edge;

inflow rail segments connected between the inflow edges of the commissure support posts; and at least one sinus support structure, each sinus support structure being disposed between but not connected to an adjacent commissure support post, wherein each sinus support structure comprises a pair of diverging side arms, each side arm being connected to the inflow rail segment near the midpoint between the adjacent commissure posts, each side arm also extending at an angle toward one of the adjacent commissure posts, each side arm terminating near, but not being connected to the adjacent commissure post.

2. The stent of claim 1, wherein a top rail is connected to and extends between the pair of diverging side arms.

3. The stent of claim 2, wherein each sinus support structure includes a central opening bounded by the top rail and the diverging side arms.

* * * * *